United States Patent [19]

Rosenfeld

[11] 4,004,599
[45] Jan. 25, 1977

[54] DENTAL FLOSS HOLDER

[76] Inventor: Marvin L. Rosenfeld, 602 Esplanade No. 205, Redondo Beach, Calif. 90277

[22] Filed: July 7, 1975

[21] Appl. No.: 593,192

[52] U.S. Cl. .............................................. 132/92 R
[51] Int. Cl.² ........................................ A61C 15/00
[58] Field of Search ................. 132/92, 91, 90, 89

[56] References Cited

UNITED STATES PATENTS

| | | | |
|---|---|---|---|
| 911,068 | 2/1909 | Perkins | 132/92 R |
| 2,554,526 | 5/1951 | Dembenski | 132/92 R |

Primary Examiner—G.E. McNeill
Attorney, Agent, or Firm—Willie Krawitz

[57] ABSTRACT

A dental floss holder with a unique locking mechanism is provided to lock a length of floss from further extension after it has been extracted from a container integral with the holder. Tension can then be applied to the floss as it is spanned across two spaced supports and wound about a button. This provides a taut span of floss which can be manipulated between the user's teeth. A cutter is provided for severence of excess floss; alternatively, the locked length of floss can be applied directly to the cutter for severence of floss.

3 Claims, 4 Drawing Figures

DENTAL FLOSS HOLDER

BACKGROUND OF THE INVENTION

This invention relates to a dental floss holder containing a supply of floss and adapted to provide an exposed section of dental floss maintained under tension for cleaning between the user's teeth.

The device functions by means of a simple locking mechanism which permits the floss to be tensioned after it has been withdrawn, and wound to expose a taut portion. Following use, the floss if unwound and severed. In prior art devices, an intricate rewinding and rethread- ing mechanism is required to tension and sever the floss.

In the present invention, a length of floss is pulled from its container thereby unwinding it from a spool. When a sufficient length has been unwound, the radial angle at which the floss is withdrawn from the spool is changed; this causes the floss to lock. Tension is applied to the locked floss as it is stretched between two supports and finally secured by wrapping it around a button. The taut floss can be manipulated between teeth.

If the floss is severed by pressure against the teeth, the severed end is unwound from the button and discarded. The portion protruding from the container is immediately ready for repositioning as previously described.

The invention will be readily understood from the drawings in which.

THE INVENTION

Figure 1:
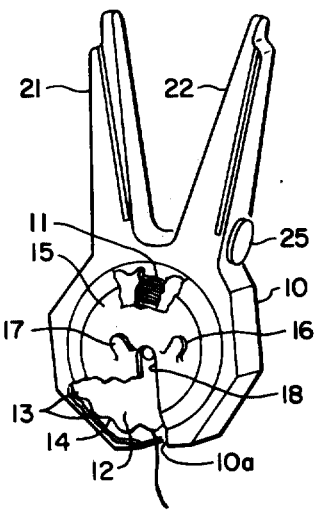
FIG. 1 is an external perspective view, partly cutaway showing the unwinding and locking mechanism of the floss holder.

The floss holder of the invention is shown in FIG. 1 and comprises a container portion 10, partially open-ended at 10a. A spool 11 of dental floss is housed in the chamber and is rotatably mounted on a toothed wheel 12 having teeth 13 and grooves 14. A removable cover 15 having a severing tabs 16, 17 is provided as a cover for the chamber; a locking slot 18 (or equivalent means such as a groove or pins) is provided on the plate.

The floss holder is provided with two spaced holder posts 21, 22 each having groove portions 23, 24 along their respective sides; the locking slot 18 is approximately aligned with one of the posts. A button 25 is mounted at the side of post 22; the floss is tensioned by passing it along grooves 23, 24 and wrapping around the button 25. Other wrapping means may be employed instead of button 25, such as a groove. In another variation, only one holder post is provided and the floss is held under tension between the user's fingers and the post.

Figure 2:
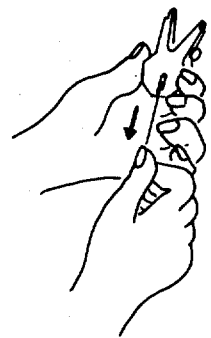
FIGS. 2 and 3 are external views partly in perspective, showing the initial unwinding of the floss and locking of the mechanism.
Figure 3:
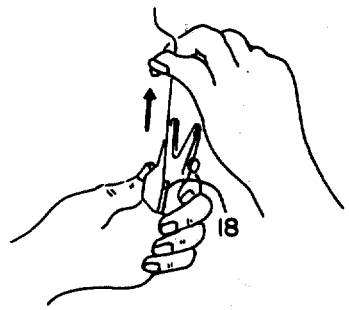
Figure 4:
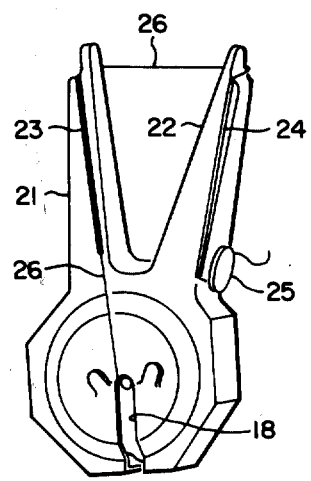
FIG. 4 is an external view, partly in perspective showing the floss holder with the floss in position ready for use.

In operation, a length of floss is unwound from the spool 11 in the direction of the arrow as shown in FIG. 2. To lock the floss and prevent further unwinding, the length of floss is pulled up along slot 18 in the direction indicated by the arrow in FIG. 3. This positioning causes the floss to contact one of the grooves 14 of the wheel 12. Any rotation of the spool 11 will now tend to move the length of floss away from its path along slot 18. Since the floss passes approximately over the center of the wheel, pulling the length of floss will cause no moment of rotation to move the wheel. If the floss passes slightly to either side of the wheel center, the friction caused by tipping the floss spool 11 upward against the cover 15 will overcome the small moment of rotation and lock the floss. In some instances, if the moment of rotation is greater than the friction of the spool against the cover, the locking slot 18 will prevent rotation of the spool by contacting the length of floss as the wheel starts to rotate.

Upon manipulation of the floss holder, the tensioned floss portion 26 can be employed to clean a user's teeth. Following cleaning, the used portion of floss is unwound and cut at severing tab 16 or 17.

The locking device of this invention employs a simple arrangement of parts to enable locking of the floss. This in turn permits a tensioned length of floss to be formed quickly and with a minimum of effort for quick use.

I claim:

1. A dental floss holder including a member having a chamber for accomodating a removable holder carrying a thread of dental floss and provided with means for removing sections of the dental floss from the holder inside the chamber and supporting the removed sections in a taut manner external of the holder and spaced from external portions of the holder to permit the taut thread to be applied to the teeth of the user; the improvement wherein the member, holder, and the thread are interrelated such that upon tension being applied to the removed section of the thread, the thread itself locks the holder in position in the chamber and prevents further with- drawal or unravelling of thread from the holder, said im- provement comprising an opening in the member leading from the chamber to enable removal of thread from the chamber, and an irregular surface portion provided on the holder in substantial alignment with said opening, said thread being compelled to interengage with said irregular surface portion in passing through said opening when external tension is applied to the thread, whereby said holder is thereupon locked and prevented from movement to unravel additional thread by the interengagement of the thread with the irregular surface portions of the holder and the wall of said opening.

2. In the dental floss holder of claim 1, the holder comprising a flanged spool having locking teeth provided about one of its flanges, and said opening in the member being provided as an elongated slot disposed radially with respect to the toothed flange on the spool, whereby removal of the thread is enabled by positioning the thread near one end of the slot in a direction out of engagement with the teeth, and locking of the thread and spool is obtained by positioning the thread near the other end of the slot and into engagement with the teeth and thereafter applying tension to the thread.

3. In the dental floss holder of claim 1, the body of said holder being provided with a pair of projecting arms for spanning the thread between the arms under tension, and means for fastening the end of the thread to the body to maintain such tension while using the holder.

* * * * *